(12) United States Patent
Gelfand et al.

(10) Patent No.: US 9,744,351 B1
(45) Date of Patent: *Aug. 29, 2017

(54) DEVICE AND METHOD FOR THE TREATMENT OF BREATHING DISORDERS AND CARDIAC DISORDERS

(71) Applicant: Respicardia, Inc., Minnetonka, MN (US)

(72) Inventors: Mark Gelfand, New York, NY (US); Howard R. Levin, Teaneck, NJ (US)

(73) Assignee: Respicardia, Inc., Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/521,647

(22) Filed: Oct. 23, 2014

Related U.S. Application Data

(63) Continuation of application No. 12/009,352, filed on Jan. 18, 2008, now Pat. No. 8,909,341.

(60) Provisional application No. 60/881,695, filed on Jan. 22, 2007.

(51) Int. Cl.
*A61N 1/05* (2006.01)

(52) U.S. Cl.
CPC .......... *A61N 1/0587* (2013.01); *A61N 1/05* (2013.01)

(58) Field of Classification Search
CPC ... A61N 1/05; A61N 1/18; A61N 1/36; A61N 1/3601; A61N 1/36114; A61B 5/4818
USPC ....................................... 607/9, 42
See application file for complete search history.

(56) References Cited

U.S. PATENT DOCUMENTS

| | | | |
|---|---|---|---|
| 4,129,125 A | 12/1978 | Lester et al. | |
| 4,702,253 A | 10/1987 | Nappholz et al. | |
| 4,827,935 A | 5/1989 | Geddes et al. | |
| 4,830,008 A | 5/1989 | Meer | |
| 5,002,067 A | 3/1991 | Berthelsen et al. | |
| 5,056,519 A | 10/1991 | Vince | |
| 5,146,918 A | 9/1992 | Kallok et al. | |
| 5,170,802 A | 12/1992 | Mehra et al. | |
| 5,199,428 A * | 4/1993 | Obel et al. | 607/44 |
| 5,265,604 A | 11/1993 | Vince | |
| 5,330,507 A * | 7/1994 | Schwartz | 607/14 |
| 5,423,865 A | 6/1995 | Bowald et al. | |
| 5,483,969 A | 1/1996 | Testerman et al. | |
| 5,485,851 A | 1/1996 | Erickson | |
| 5,524,632 A | 6/1996 | Stein et al. | |
| 5,578,061 A * | 11/1996 | Stroetmann et al. | 607/4 |
| 5,922,014 A | 7/1999 | Warman et al. | |
| 5,938,694 A | 8/1999 | Jaraczewski et al. | |
| 6,006,134 A * | 12/1999 | Hill et al. | 607/9 |

(Continued)

FOREIGN PATENT DOCUMENTS

| | | |
|---|---|---|
| DE | 10103288 A1 | 8/2002 |
| WO | 2008092246 A1 | 8/2008 |

OTHER PUBLICATIONS

Redline, Susan et al., Beyond the Fat Boy, Journal of Applied Physiology 2005, vol. 99: pp. 1243-1244.

(Continued)

*Primary Examiner* — Christopher D Koharski
*Assistant Examiner* — Roland Dinga
(74) *Attorney, Agent, or Firm* — Frank P. Piskolich

(57) ABSTRACT

The present invention is related to an implantable medical device for treating breathing disorders and cardiac disorders by delivering stimulation energy to the phrenic nerve, hypoglossal nerves and cardiac muscle tissues.

10 Claims, 4 Drawing Sheets

(56) References Cited

U.S. PATENT DOCUMENTS

| | | | |
|---|---|---|---|
| 6,132,384 A | 10/2000 | Christopherson et al. | |
| 6,212,435 B1 | 4/2001 | Lattner et al. | |
| 6,266,564 B1 | 7/2001 | Hill et al. | |
| 6,314,324 B1 | 11/2001 | Lattner et al. | |
| 6,360,740 B1 | 3/2002 | Ward et al. | |
| 6,415,183 B1 | 7/2002 | Scheiner et al. | |
| 6,449,507 B1 | 9/2002 | Hill et al. | |
| 6,463,327 B1 | 10/2002 | Lurie et al. | |
| 6,532,388 B1 | 3/2003 | Hill et al. | |
| 6,537,228 B1 | 3/2003 | Lambert | |
| 6,542,774 B2 | 4/2003 | Hill et al. | |
| 6,587,726 B2 | 7/2003 | Lurie et al. | |
| 6,589,188 B1 | 7/2003 | Street et al. | |
| 6,641,542 B2 | 11/2003 | Cho et al. | |
| 6,684,101 B2 | 1/2004 | Daum | |
| 6,718,208 B2 | 4/2004 | Hill et al. | |
| RE38,705 E | 2/2005 | Hill et al. | |
| 6,881,192 B1 | 4/2005 | Park | |
| 6,890,306 B2 | 5/2005 | Poezevera | |
| 6,928,324 B2 | 8/2005 | Park et al. | |
| 6,934,583 B2 | 8/2005 | Weinberg et al. | |
| 6,937,903 B2 | 8/2005 | Schuler et al. | |
| 6,964,641 B2 | 11/2005 | Cho et al. | |
| 7,025,730 B2 | 4/2006 | Cho et al. | |
| 7,070,568 B1 | 7/2006 | Koh | |
| 7,077,132 B2 | 7/2006 | Berthon-Jones | |
| 7,082,331 B1 | 7/2006 | Park et al. | |
| 7,094,207 B1 | 8/2006 | Koh | |
| 7,155,278 B2 | 12/2006 | King et al. | |
| 7,179,229 B1 | 2/2007 | Koh | |
| 7,184,829 B2 | 2/2007 | Hill et al. | |
| 7,200,442 B1 | 4/2007 | Koh et al. | |
| 7,212,862 B2 | 5/2007 | Park et al | |
| 7,223,244 B1 | 5/2007 | Koh | |
| 7,225,019 B2 | 5/2007 | Jahns et al. | |
| 7,225,021 B1 | 5/2007 | Park et al. | |
| 7,245,971 B2 | 7/2007 | Park et al. | |
| 7,269,457 B2 | 9/2007 | Shafer et al. | |
| 7,269,459 B1 | 9/2007 | Koh | |
| 7,277,757 B2 | 10/2007 | Casavant et al. | |
| 7,340,302 B1 | 3/2008 | Falkenberg et al. | |
| 7,357,775 B1 | 4/2008 | Koh | |
| 7,361,146 B1 | 4/2008 | Bharmi et al. | |
| 7,363,086 B1 | 4/2008 | Koh et al. | |
| 7,371,220 B1 | 5/2008 | Koh et al. | |
| 7,813,805 B1 | 10/2010 | Farazi | |
| 2001/0003799 A1 | 6/2001 | Boveja | |
| 2002/0049479 A1* | 4/2002 | Pitts | 607/42 |
| 2002/0128563 A1 | 9/2002 | Carlson et al. | |
| 2003/0078078 A1* | 4/2003 | Weinberg et al. | 607/9 |
| 2003/0088244 A1 | 5/2003 | Swanson et al. | |
| 2003/0195571 A1 | 10/2003 | Burnes et al. | |
| 2005/0043765 A1 | 2/2005 | Williams et al. | |
| 2005/0085734 A1 | 4/2005 | Tehrani | |
| 2005/0085865 A1 | 4/2005 | Tehrani | |
| 2005/0085866 A1 | 4/2005 | Tehrani | |
| 2005/0085867 A1 | 4/2005 | Tehrani et al. | |
| 2005/0085868 A1 | 4/2005 | Tehrani et al. | |
| 2005/0085869 A1 | 4/2005 | Tehrani et al. | |
| 2005/0165457 A1 | 7/2005 | Benser et al. | |
| 2005/0197588 A1 | 9/2005 | Freeberg | |
| 2005/0240240 A1 | 10/2005 | Park et al. | |
| 2005/0288729 A1 | 12/2005 | Libbus et al. | |
| 2006/0030894 A1 | 2/2006 | Tehrani | |
| 2006/0036294 A1 | 2/2006 | Tehrani | |
| 2006/0084060 A1 | 4/2006 | Nagahama et al. | |
| 2006/0122662 A1 | 6/2006 | Tehrani et al. | |
| 2006/0142815 A1 | 6/2006 | Tehrani et al. | |
| 2006/0149334 A1 | 7/2006 | Tehrani et al. | |
| 2006/0155341 A1 | 7/2006 | Tehrani et al. | |
| 2006/0167523 A1 | 7/2006 | Tehrani et al. | |
| 2006/0229677 A1 | 10/2006 | Moffitt et al. | |
| 2006/0247729 A1 | 11/2006 | Tehrani et al. | |
| 2007/0021795 A1 | 1/2007 | Tehrani | |
| 2007/0118183 A1 | 5/2007 | Gelfand et al. | |
| 2007/0156199 A1 | 7/2007 | Koh et al. | |
| 2007/0260285 A1 | 11/2007 | Libbus et al. | |
| 2008/0154330 A1 | 6/2008 | Tehrani et al. | |
| 2008/0161878 A1 | 7/2008 | Tehrani et al. | |
| 2008/0167695 A1 | 7/2008 | Tehrani et al. | |
| 2008/0177347 A1 | 7/2008 | Tehrani et al. | |
| 2008/0183239 A1 | 7/2008 | Tehrani et al. | |
| 2008/0183240 A1 | 7/2008 | Tehrani et al. | |
| 2008/0183254 A1 | 7/2008 | Bly et al. | |
| 2008/0183259 A1 | 7/2008 | Bly et al. | |
| 2008/0183264 A1 | 7/2008 | Bly et al. | |
| 2008/0188903 A1 | 8/2008 | Tehrani et al. | |
| 2008/0188904 A1 | 8/2008 | Tehrani et al. | |
| 2008/0234694 A1 | 9/2008 | Stegfeldt et al. | |
| 2009/0088827 A1 | 4/2009 | Tockman et al. | |
| 2010/0249630 A1 | 9/2010 | Droitcour et al. | |
| 2011/0060380 A1 | 3/2011 | Gelfand et al. | |

OTHER PUBLICATIONS

Esler, Murray et al., Is Obstructive Sleep Apnea the Cause of Sympathetic Nervous Activation in Human Obesity?, Journal of Applied Physiology 2006, vol. 100, pp. 11-12.

Caples, Sean M. et al., Influence of Cardiac Function and Failure on Sleep-Disordered Breathing, Journal of Applied Physiology 2005, vol. 99, pp. 2433-2439.

Punjabi, Naresh M. et al., Disorders of Glucose Metabolism in Sleep Apnea, Journal of Applied Physiology 2005, vol. 99, pp. 1998-2007.

Leuenberger, Urs A et al., Hypoxia Augments Apnea-Induced Peripheral Vasoconstriction in Humans, Journal of Applied Physiology 2001, vol. 90, pp. 1516-1522.

Oliven, Arie et al., Upper Airway Response to Electrical Stimulation of the Genioglossus in Obstructive Sleep Apnea, Journal of Applied Physiology 2003, vol. 95, pp. 2023-2029.

Parati, Gianfranco et al., Sleep Apnea: Epidemiology, Pathophysiology, and Relation to Cardiovascular Risk, Am Journal Physiological Society 2007, vol. 293, pp. R1671-R1683.

Gottfried, Stewart B. et al., Effects of Phrenic Stimulation on Upper Airway Resistance in Anesthetized Dogs, Am Physiological Society 1983, 0161-7567/83, pp. 419-426.

Planas, Roque F. et al., Diaphragmatic Pressures: Transvenous vs. Direct Phrenic Nerve Stimulation, Am Physiological Society 1985, 0161-7567/85, pp. 269-273.

Series, F. et al., Site of Phrenic Nerve Stimulation-Induced Upper Airway Collapse: Influence of Expiratory Time, Journal of Applied Physiology 2002, vol. 92, pp. 665-671.

Kingma, John G. Jr. et al., Neuromodulcation Therapy Does Not Influence Blood Flow Distribution or Left-Ventricular Dynamics During Acute Myocardial Ischemia, Autonomic Neuroscience: Basic and Clinical 91 (2001) pp. 47-54.

Linderoth, Bengt, MD, PHD et al., Mechanisms of Spinal Cord Stimulation in Painful Syndromes: Role of Animal Models, American Academy of Pain Medicine, vol. 7, No. S14-S26, 2006.

Tanaka, Satoshi et al., Mechanisms of Sustained Cutaneous Vasodilation Induced by Spinal Cord Stimulation, Autonomic Neuroscience: Basic and Clincal 114 (2004) pp. 55-60.

Lorenzi-Filho, Geraldo et al., Cheyne-Stokes Respiration in Patients with Congestive Heart Failure: Causes and Consequences, Clincs 2005: 60(4):333-44.

Brack, Thomas, Cheyne-Stokes Respiration in Patients with Congestive Heart Failure, Swiss Med Wkly 2003; 133:605-610, www.smw.ch.

Yumino, Dai et al., Central Sleep Apnea and Cheyne-Stokes Respiration, Proceedings of the American Thoracic Society, 2008, vol. 5, pp. 226-236.

Garrido-Garcia, H. et al., Treatment of Chronic Ventilatory Failure Using a Diaphragmatic Pacemaker, Spinal Cord (1998) 36, 310-314.

Diedrichs, Holger et al., Symptomatic Relief Precedes Improvement of Myocardial Blood Flow in Patients Under Spinal Cord Stimulation, BioMed Central, 2005, pp. 1-7.

(56) References Cited

OTHER PUBLICATIONS

Kaneko, S. et al., A New Approach to Respiratory Assist for Phrenic Nerve Paralysis, Trans Am Soc. Artif Intern Organs, 1985, vol. XXI, pp. 301-304.
Macintyre, Neil R., MD, Setting the Frequency-Tidal Volume Pattern, www.rcjournal.com/contents/03.02/03.02.0266.asp.
Kohnlein, T. et al., Central Sleep Apnea Syndrome in Patients with Chronic Heart Disease: A Critical Review of the Current Literature, Thorax 2002; 57:547-554.
Javaheri, Shahrokh, MD, Central Sleep Apnea in Congestive Heart Failure: Prevalence, Mechanisms, Impact, and Therapeutic Options, Seminars in Respiratory and Critical Care Medicine, 2005, vol. 26, No. 1.
Dobelle, William H., Use of Breathing Pacemakers to Suppress Intractable Hiccups of up to Thirteen Years Durationg, ASAIO Journal 1999, pp. 524-525.
Series, Frederic, Assessment of Upper Airway Dynamics in Awake Patients with Sleep Apnea Using Phrenic Nerve Stimulation, Am Journal Respir Crit Care Med, 2000, vol. 162., pp. 795-800.
Bilgutay, A.M. et al., Augmented Ventilation by Synchronous Phrenic Nerve Stimulation, Trans. Amer. Soc. Artif. Int. Organs, 1970, vol. XVI, pp. 213-217.
Yasuma, Sumihiko et al., Eight-Year Follow-Up Study of a Patient with Central Alveolar Hypoventilation Treated with Diaphragm Pacing, Respiration, 1998; 65:313-316.
Handa, Y. et al., Basic Studies on Electrophrenic Respiration Part 2—Assisted Ventilation by the Synchronous Electrophrenic Respirator, Medical and Biological Engineering, Jul. 1976.
Kimura, M. et al., A Heart-Rate-Responsive Diaphragm Pacemaker, Med. & Biol. Eng. & Comput., 1987, 25. 458-462.
Kimura, M. et al., Heart Rate and Body Temperature Sensitive Diaphragm Pacing, Med. & Biol. Eng. & Comput. 1992, 30, 155-161.
Kimura, M. et al., Addition to an RF-Coupled Phrenic Nerve Stimulator Implant to Provide Outward Transmission of Body Temperature, Med. & Biol. Eng. & comput. 1986, 24, 659-661.
Taira, TAkaomi, MD, Ph. D. et al., Phrenic Nerve Stimulation for Diaphragm Pacing with a Spinal Cord Stimulator, Elsevier Science, Surg Neurol, 2003; 59:128-32.
Chatfield, Paul O. et al., Role of Pulmonary Proprioceptive Reflexes in Suppression of Spontaneous Breathing During Electrophrenic Respiration, Dept. of Physiology, Harvard Medical School, and Dept. of Physiology, Harvard School of Public Health, vol. 163.
Sarnoff, Stanley J. et al., Electrophrenic Respiration. III. Mechanism of the Inhibition of Spontaneous Respiration, Dept. of Physiology, Harvard School of Public Health, 1948, vol. 155. pp. 203-207.
Sarnoff, Stanley J. et al., Electrophrenic Respiration IV. The Effectiveness of Contralateral Ventilation During Activity of One Phrenic Nerve, Dept. of Physiology, Harvard School of Public Health, 1949, pp. 929-937.

Stemmer, Edward A. MD et al., Diaphragmatic Pacing in the Treatment of Hypoventilation Syndrome, Journal of Thoracic and Cardiovascular Surgery, vol. 54, No. 5, 1967, pp. 649-657.
Furman, Seymour, MD et al., Transvenous Stimulation of the Phrenic Nerves, Journal of Thoracic and Cardiovascular Surgery, vol. 62, No. 5, 1971, pp. 743-751.
Aiyar, Harish et al., Diaphragm Pacing for Chronic Respiratory Insufficient, CRC Press, LLC, 2001, Chapter 9.
Oliven, Arie et al. Upper Airway Response to Electrical Stimulation of the Genioglossus in Obstructive Sleep Apnea, Journal of Applied Physiology, 95:2023-2029, 2003.
Javaheri, Shahrokh, MD, Acetazolamide Improves Central Sleep Apnea in Heart Failure Pulmonary Service, Department of Veterans Affairs Medical Center, and Department of Medicine, University of Cincinnati College of Medicine, Cincinnati, Ohio Am J Respir Crit Care Med vol. 173. pp. 234-237, 2006, Jul. 5, 2005.
Vaseghi, et al., Beyond Coronary Sinus Angiography: The Value of Coronary Arteriography and Identification of the Pericardiophrenic Vein During Left Ventricular Lead Placement, PACE, 2005, vol. 28.
Leung, Richard S. T. et al., Influence of Cheyne-Stokes Respiration on Cardiovascular Oscillations in Heart Failure, Am J Respir Crit Care Med, 2003, vol. 167. pp. 1534-1539.
Escher, Doris J.W., Clinical control of Respiration by Transvenous Phrenic Pacing, Trans. Amer. Soc. Artif. Int. Organs., vol. XIV, 1968.
Levy, T. et al., A Comparison Between Passive and Active Fixation Leads in the Coronary Sinus for Biatrial Pacing, The European Society of Cardiology 2000.
Javaheri, Shahrokh M.D., CPAP Should Not Be Used for Central Sleep Apnea in Congestive Heart Failure Patients, Journal of Clinical Sleep Medicine, vol. 2, No. 4, 2006.
Hall, Michael J. et al., Cycle Length of Periodic Breathing in Patients with and without Heart Failure, Am. J. Respir. Crit. Care Med vol. 154. pp. 376-381, 1996.
Hasdemir, Can MD et al., Jpn Heart J, vol. 44 No. 3, 2003.
Schauerte, Patrick et al., Catheter Stimulation of Cardiac Parasympathetic Nerves in Humans: A Novel Approach to the Cardiac Autonomic Nervous System, American Heart Association 2006.
Shaul, Donald B., et al., Thoracoscopic Placement of Phrenic Nerve Electrodes for Diaphragmatic Pacing in Children, Journal of Pediatric Surgery, vol. 37, No. 7 pp. 974-978, 2002.
Plisiene, Jurgita et al., Selective Transvascular Stimulation of Cardiac Autonomic Nerves: A Novel Technique, Biomedicine vol. 2 No. 1, Jul. 2002.
Arzt, Michael et al., Treatment of Sleep Apnea in Heart Failure, Am J Respir Crit Care Med vol. 173. pp. 1300-1308, 2006.
Thoma, H. et al., The Vienna Phrenic Pacemaker, Longterm Data of Failures, 1993.
Ishii, Kiyoshi, Effects of Bilateral transvenous diaphragm pacing on hemodynamic function in patients after cardiac operations, 1990.

* cited by examiner

DEVICE AND METHOD FOR THE TREATMENT OF BREATHING DISORDERS AND CARDIAC DISORDERS

CROSS REFERENCE TO RELATED CASES

The present case claims the benefit of U.S. Provisional Application 60/881,695 filed Jan. 22, 2007 entitled Transvenous Stimulation of Hypoglossal Nerve to Treat Central and Obstructive Sleep Apnea. The disclosure of the provisional application is incorporated by reference.

FIELD OF THE INVENTION

An implantable medical device and a method carried out with an implantable medical device for the treatment of sleep apnea and for the treatment of sleep apnea in patients with cardiac disorders.

BACKGROUND OF THE INVENTION

Sleep apnea (SA) is a disease state in which the patient exhibits periodic breathing. Sleep apnea is typically characterized as either "obstructive" (OSA) or "central" (CSA). Many patients exhibit the disorder in both of its forms, OSA and CSA. OSA is traditionally treated by attempting to maintain patency of the upper airway. CSA is traditionally treated by stimulation of the diaphragm. Sleep apneas occur with high frequency in patients with cardiac rhythm disorders that might be treated with bradycardia treatment or biventricular pacemakers.

SUMMARY

The present invention includes a method, device, and system for treatment of SA breathing. The system includes one or more transvenous leads coupled to an implanted medical device, where one lead system is positioned to stimulate a muscle group. An additional lead system is positioned to stimulate at least one nerve. In an alternative embodiment of the device, the two lead systems both stimulate nerves. In this alternative embodiment, one set of nerves leads to muscle contraction and the other set of nerves do not lead to muscle contraction but they locally alter the "tone" of the nervous system.

DETAILED DESCRIPTION OF THE INVENTION

The nervous system (NS) is exceedingly complex. Two main components of the NS are the sympathetic NS and the parasympathetic NS. It is widely held that these two systems counteract each other and a homeostatic balance is achieved between them. It is recognized that the relative activation of the two systems results in a "tone" that that varies between waking and sleeping states.

Without elucidating a complete mechanism of action, the inventors completed a course of experimentation that suggests to them that transvenous stimulation near the base of the tongue, near the location of the hypoglossal nerves, increases airflow during apnea with out actually provoking activation of muscle tissue near the stimulation site. Applicants believe that this sub-threshold stimulation alters "tone". It should be understood that the measurement of tone is fraught with technical difficulties; However, the inventors believe that the periodic and episodic application of electrical currents at voltages and currents far below the levels required for evoked muscle contraction of tissue near the tongue are responsible for an increase in the diameter of the airway passages and increase ventilation in patients. The inventors believe that episodic background simulation may increase the otherwise prevailing level of tone and that this level of stimulation is compatible with restful sleep and will not arouse a sleeping patient. In each embodiment of the inventors' system low-level stimulation is travenously delivered to nerves and muscles near the hypoglossal tissues of a patient.

Figure 1:
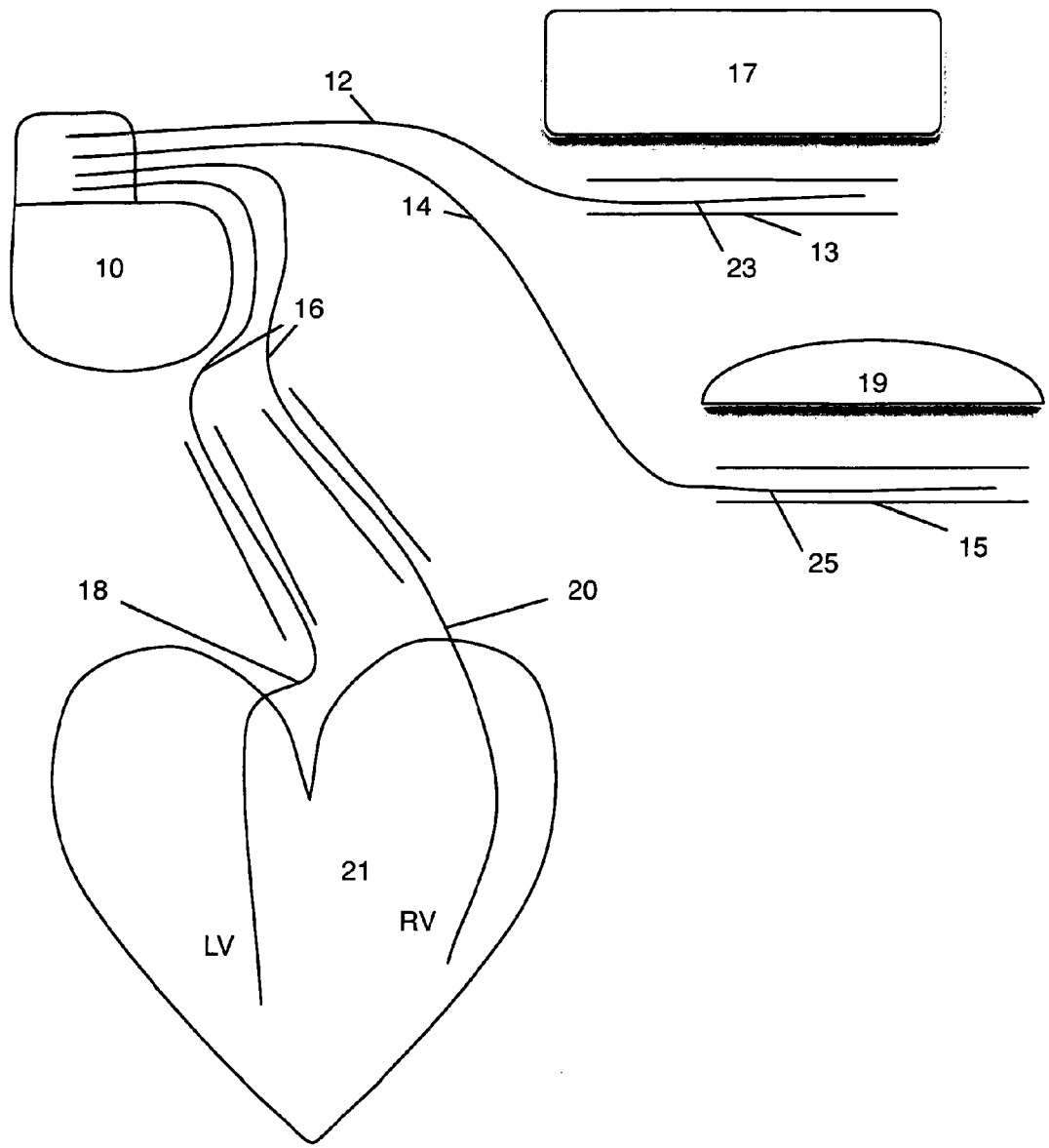
FIG. 1 depicts the system in schematic form.

FIG. 1 depicts an implanted medical device 10 (IMD) of the type necessary to carry out the invention. The IMD 10 is coupled to a first transvenous lead system 12 located in the area of the tongue near the hypoglossal nerves represented schematically at reference numeral 17 and placing stimulation electrodes typified by electrode 23 in a vein or artery 13 near the hypoglossal nerves 17. A second lead system 14 couples the IMD 10 transvenously to the phrenic nerve and diaphragm represented schematically at reference numeral 19. Once again stimulation electrodes are placed near the phrenic nerve as indicated schematically at reference numeral 25. A third lead system 16 places a pacing lead 20 in the right ventricle RV and a pacing lead 18 positioned to stimulate the left ventricle LV of the heart 21.

The IMD 10 contains conventional circuitry to detect the patients R-wave and impedance plythesmographic detectors to find the mid breath point in the respiration cycle. The IMD 10 also contains an activity sensor to measure the activity level of the patient. This activity sensor may be used to detect periods of sleep. These sense amplifiers, stimulation pulse generators, activity monitors, and impedance monitors are structures that are not described in detail as they are well known to those skilled in this art.

Pacing Embodiment

The transvascular subthreshold low level stimulation of the hypoglossal tissues near the upper airways may be combined with conventional bradycardia pacing therapies. Applicants describe a device that combines low-level transvascular stimulation with a conventional pacing regime or modality. Although the invention is applicable to both biventricular lead placements as well as cardiac defibrillator lead placements, the invention is described in the context of a biventricular demand mode pacemaker. It must be understood that other bradycardia and tachycardia treatment modalities are contemplated and are within the scope of the claims. The choice of the depicted modality is selected for simplicity and because it is indicated for patients likely to also suffer from sleep apnea.

During periods of pacing support of the patient's rhythm the IMD 10 will also delivers stimulation energy to the hypoglossal tissues via the transvenous lead 12. The stimulation energy delivered may be continuous or intermittent at an appropriate relatively low frequency duty cycle.

At times when the patient's detected activity is low, the IMD may deliver background stimulation from an appropriate pulse generator within the IMD 10 through the lead system 12 at a level insufficient to arouse the patient from sleep.

Figure 2:
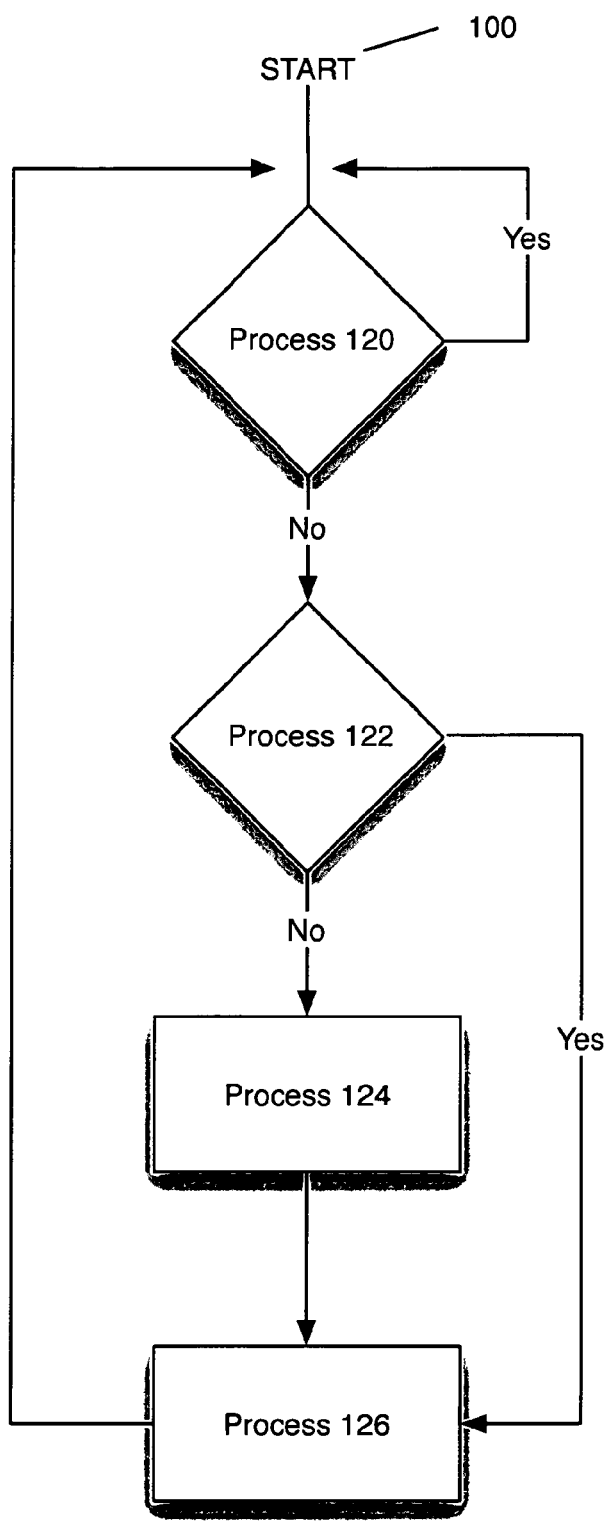
FIG. 2 depicts a process carried out in the implanted device.

FIG. 2 is a flowchart depicting representative implementation of the integration of very low energy transvascular hypoglossal stimulation with brady pacing. The process starts with block 100. In decision block 120 the presence or absence of an R-wave is determined with a sense amplifier within the IMD 10. If an R-wave is detected (yes in process 120), the process 120 resets the pacing escape interval timer and returns to the start of R-wave detection process 120. If an R-wave does not occur within an escape interval (no in process 120), the process moves to process 122 where patient activity is monitored. If the patient is inactive (no in process 122), perhaps asleep, and in need of ventricular stimulation, then the processes 124 activates the low level hypoglossal tissues via lead system 12 while process 126 activates the biventricular pulse generators to delivery stimulation on leads 18 and 20. In this fashion the patient receives the low level hypoglossal stimulation in phase with pacing therapy. Other variations in stimulation patterns are possible as well.

Respiration Embodiment

The IMD 10 is equipped to detect respiration and deliver stimulation to the phrenic nerve via lead system 14 at times and stimulation magnitudes to "hold" the breath of a patient. This breath holding attribute tends to decrease breathing rate and has been proposed by the inventors as a treatment for central sleep apnea.

Figure 3:
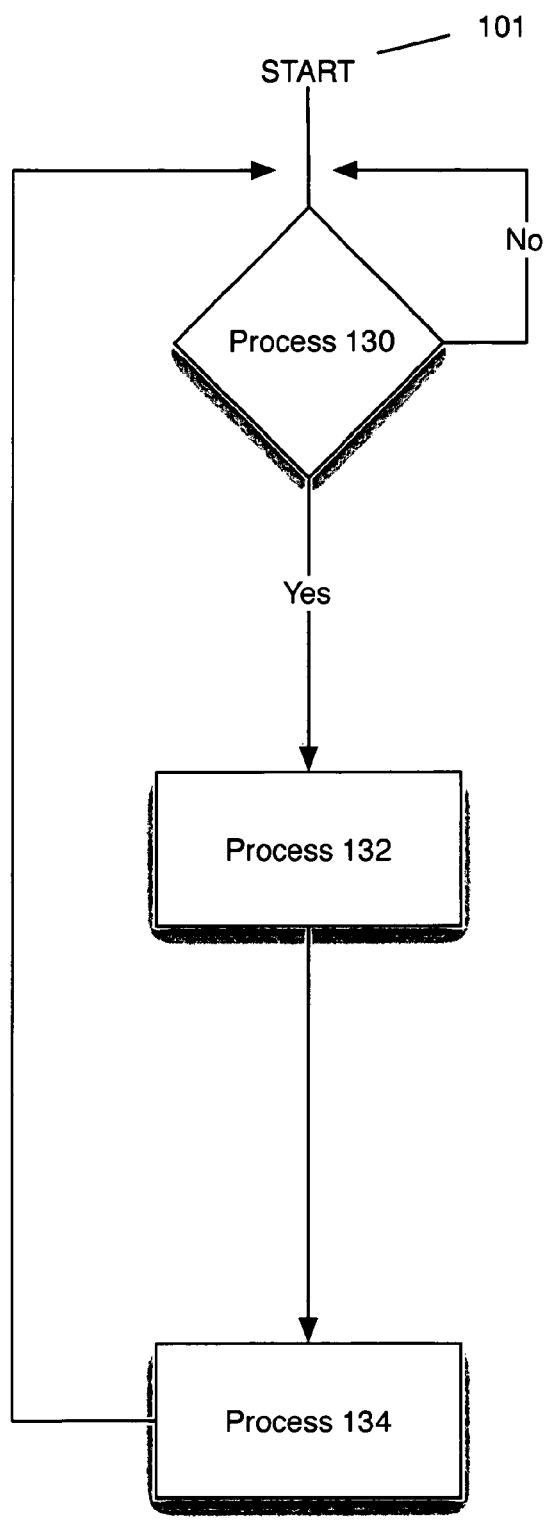
FIG. 3 depicts a process carried out in the implanted device.

In this embodiment low-level electrical stimulation of the tissues near the hypoglossal nerve is invoked and delivered at the time that phrenic nerve receives stimulation. FIG. 3 depicts a representative implementation of a software process carried out within the IMD 10 to treat a patient. In the start process 101 the IMD 10 turns on the respiration sensor system, and in process 130 the IMD finds the mid-breath point. If appropriate (yes in process 130), the IMD enters process 132 where pulse generators within the IMD deliver phrenic nerve stimulation via lead system 14 in synchrony with the mid breath respiration point. The device moves to process 134 where low-level hypoglossal stimulation is delivered via lead system 12. In this fashion low-level electrical energy is delivered to the upper airway to improve patency during a breath. In this way the invention overcomes limitations of prior art that require:
1. surgical placement of nerve stimulation electrodes on the nerve
2. synchronized stimulation that requires contraction of selected airway muscles prior and during natural inspiration phase of the breath
3. discomfort to the patient caused by stimulation of small muscles in the head and neck Stimulation pulses are applied during the inspiratory phase of the breath. The inspiratory phase can be initiated by the patient or by the logic of the IMD in response to sensed apnea. Stimulation of hypoglossal nerve can be applied in synchrony with stimulation of the phrenic nerve. Stimulation of the hypoglossal nerve can be applied slightly ahead of the stimulation of the phrenic nerve to prevent airway collapse that is a known side effect of phrenic stimulation.

Another variation of the respiration embodiment involves a step-wise sequence including the steps of:
a. locating a transvenous stimulation electrode near the hypoglossal nerve;
b. locating a transvenous stimulation electrode near the phrenic nerve;
c. detecting the respiration of the patient;
d. supplying stimulation to the hypoglossal transvenous stimulation electrode to maintain patency of the airway during a breath;
f. supplying stimulation to the phrenic nerve transvenous stimulation electrode to extend the duration of a breath.

Yet another variation of the respiration embodiment involves a step-wise sequence including the steps of:
a. locating a transvenous stimulation electrode near the hypoglossal nerve;
b. locating a transvenous stimulation electrode near the phrenic nerve;
c. detecting the respiration of the patient;
d. supplying stimulation to the hypoglossal transvenous stimulation electrode to maintain patency of the airway during a breath;
e. supplying stimulation to the phrenic nerve transvenous stimulation electrode to extend the duration of a breath;
f. supplying the stimuli of d. and e. sequentially to initiate a breath.

Figure 4:
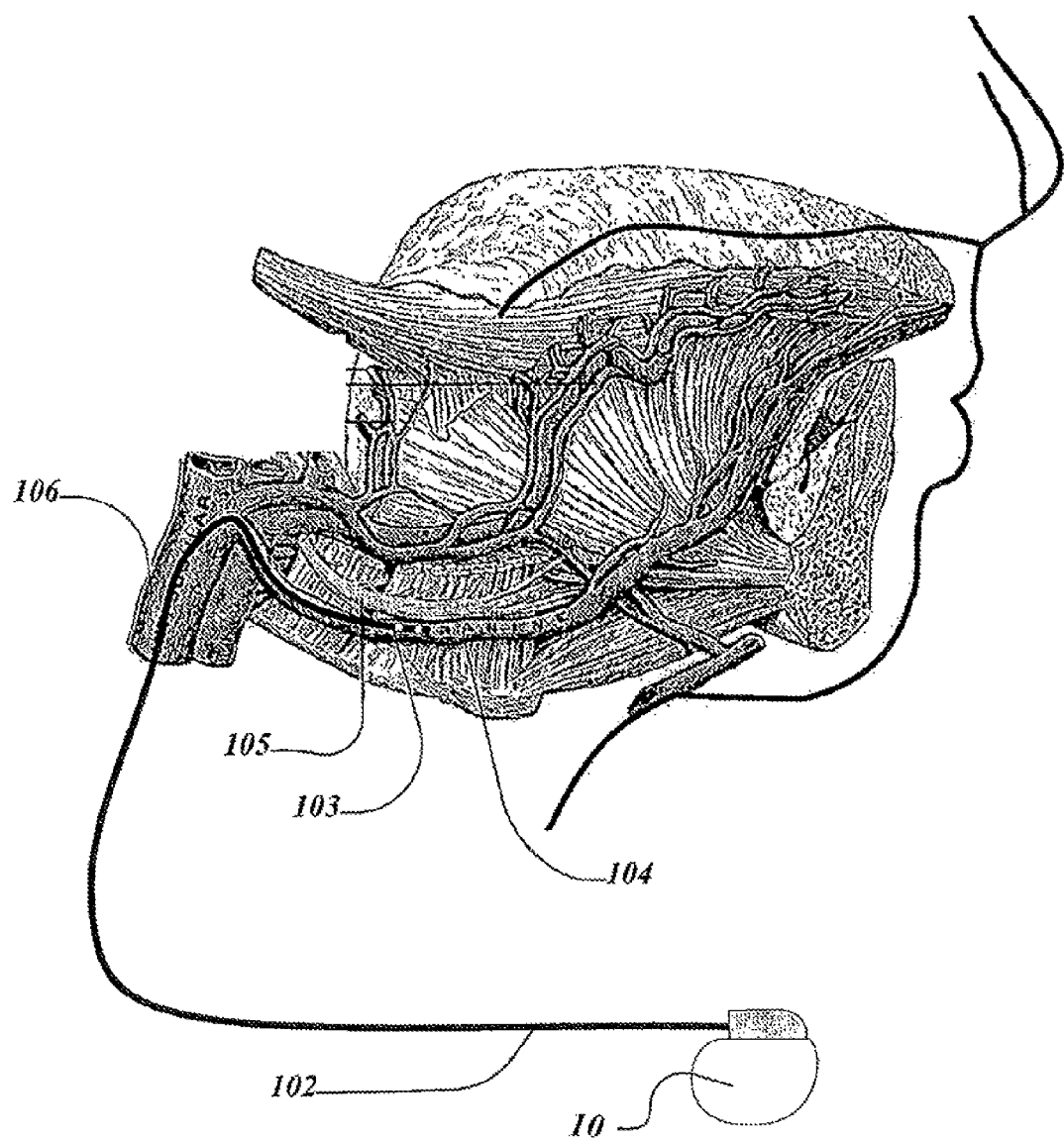
FIG. 4 depicts a device in accordance with embodiments of the invention.

FIG. 4 is a schematic diagram showing an implanted medical device (IMD) 10 that can be an IPG implantable pulse generator implanted in a patient's chest for carrying out a therapeutic stimulation of hypoglossal nerve 105. The device 10 is equipped with the lead 102 that transvenously places the electrode 103 in the ranine vein 104. In this embodiment there are two electrodes for bipolar stimulation.

The lead 102 passes through the jugular vein 106. The IMD 10 can be equipped with other stimulation and sensing leads such as: leads to stimulate phrenic nerve, leads to pace the heart, leads to apply defibrillation pulses, leads to sense respiration. The IMD is equipped with embedded logic that allows sensing of respiratory activity and application of synchronized stimulation pulses to electrodes.

What is claimed is:
1. An implantable medical device for treating a patient comprising;
   a. a stimulator configured to provide electrical stimulation to a first lead system and a second lead system,
   b. said first lead system configured to transvenously place a stimulation electrode in a ranine vein near the patient's hypoglossal nerve and including a processor configured to deliver electrical stimulation to the electrode in the ranine vein near the patient's hypoglossal nerve;
   c. said second lead system configured to transvenously place a stimulation electrode near the patient's phrenic nerve and wherein the processor is further configured to deliver electrical stimulation to the electrode near the patient's phrenic nerve; and
   d. the stimulator being configured to provide the electrical stimulation to the first lead system slightly before applying electrical stimulation to the second lead system.

2. The device of claim 1, wherein said stimulator is configured to supply sub threshold stimulation periodically to said first lead system to alter hypoglossal tone to a value near the value of tone during the awake state.

3. The device of claim 1, wherein said stimulator is configured to supply sub threshold stimulation periodically to said first lead system to alter tone where the level of sub threshold stimulation is selected not to arouse the patient.

4. The device of claim 1, wherein said stimulator is configured to supply sub threshold stimulation periodically to said first lead system to elevate upper airway muscle tone where level of sub threshold stimulation is selected such that the patient is not aware of stimulation while patient is awake.

5. The device of claim 1, wherein the stimulator is configured to provide the electrical stimulation to the second lead system at a defined interval.

6. An implantable medical device for treating a patient comprising:
   a. a stimulator configured to provide electrical stimulation to a lead system that includes a stimulation electrode: and
   b. the lead system configured to transvenously place the stimulation electrode in a lingual vein near the patient's hypoglossal nerve and including a processor configured to deliver electrical stimulation to the electrode in the lingual vein near the patient's hypoglossal nerve;
   c. wherein the stimulator is configured to stimulate the hypoglossal nerve from the lingual vein.

7. The device of claim 6, wherein the stimulator is configured to supply sub threshold stimulation periodically to the lead system to alter hypoglossal tone to a value near the value of tone during the awake state.

8. The device of claim 6, wherein the stimulator is configured to sub threshold stimulation periodically to the lead system to alter tone where the level of sub threshold stimulation is selected not to arouse the patient.

9. The device of claim 6, wherein said stimulator is configured to supply sub threshold stimulation periodically to the lead system to elevate upper airway muscle tone where level of sub threshold stimulation is selected such that the patient is not aware of stimulation while patient is awake.

10. The device of claim 6, further comprising a second lead system configured to transvenously place a stimulation electrode near the patient's phrenic nerve and wherein the processor is further configured to deliver electrical stimulation to the electrode near the patient's phrenic nerve; and the stimulator being configured to provide the electrical stimulation to the lead system configured to transvenously place the stimulation electrode in a lingual vein slightly before applying electrical stimulation to the second lead system.

* * * * *